United States Patent
Tieu et al.

(10) Patent No.: US 8,679,039 B2
(45) Date of Patent: Mar. 25, 2014

(54) ULTRASONIC DEVICE WITH INTEGRATED SPECIMEN DISPENSER

(75) Inventors: Hieu Tieu, San Jose, CA (US); Yuchen Zhou, San Jose, CA (US); Chao Uei Wahng, Fremont, CA (US)

(73) Assignee: La Pierres, Inc., San Jose, CA (US)

( * ) Notice: Subject to any disclaimer, the term of this patent is extended or adjusted under 35 U.S.C. 154(b) by 656 days.

(21) Appl. No.: 12/925,017

(22) Filed: Oct. 12, 2010

(65) Prior Publication Data
US 2012/0089079 A1    Apr. 12, 2012

(51) Int. Cl.
*A61H 23/00*    (2006.01)
(52) U.S. Cl.
USPC .............................................. 601/2; 601/17
(58) Field of Classification Search
USPC ........... 601/2, 17, 18, 46, 134, 135, 136, 137, 601/138; 604/22, 58, 264
See application file for complete search history.

(56) References Cited

U.S. PATENT DOCUMENTS

| 7,427,273 | B2 * | 9/2008 | Mitsui ............................... 601/2 |
| 2003/0171702 | A1 * | 9/2003 | Thompson et al. ............. 601/72 |
| 2006/0149169 | A1 |  7/2006 | Nunomura et al. |
| 2006/0276731 | A1 * | 12/2006 | Thiebaut et al. ............... 601/112 |
| 2009/0318853 | A1 | 12/2009 | Reed et al. |

\* cited by examiner

*Primary Examiner* — Quang D Thanh
(74) *Attorney, Agent, or Firm* — Dahyee Law Group; Leon E. Jew

(57) ABSTRACT

This application teaches a novel ultrasonic skin care device with a built-in specimen containment and a dispensing mechanism to enable easy application of the specimen for hygiene operation of the device for skin beautification purpose. The device provides portability for usage anywhere and anytime and provides a flexibility of multi-purpose skin care treatment with a unique design of multiple specimen containment structures.

15 Claims, 2 Drawing Sheets

ULTRASONIC DEVICE WITH INTEGRATED SPECIMEN DISPENSER

FIELD OF THE INVENTION

The present invention relates generally to ultrasonic technology. More particularly, it relates to a novel ultrasonic skin care device with a built-in specimen containment and a dispensing mechanism to enable easy application of the specimen for hygiene operation of the device for skin beautification purpose.

BACKGROUND OF THE INVENTION

Ultrasound method used for skin care and beautification has been long demonstrated and realized in commercial products and therapeutic devices. The following listed documents are the references which are most relevant to the subject matter of the present invention: (1) Y. Mitsu, "Skin beautification cosmetic system using iontophoresis device, ultrasonic facial stimulator, and cosmetic additive", U.S. Pat. No. 7,427,273 B2 (2008); (2) M. Nunomura, and T. Oba, "Ultrasound applying skin care device", Pub. No. US 2006/0149169 (2006); (3) U. Motoyoshi, "ULTRASONIC FACIAL AND BEAUTY APPLIANCE", Pub. No. JP2007050204 (A) (2007); (4) H. Hisao, "ULTRASONIC FACE MASSAGER", Pub. No. JP2001314473 (A) (2001); (5) J. Reed, and et al, "Ultrasound based cosmetic therapy method and apparatus", Pub. No. US 2009/0318853 (2009); and (6) FaceMate 330 Ultrasonic Face and Skin Massager from Balkowitsch Enterprises (www.balkowitsch.com).

FIG. 1 is a schematic diagram illustrating a generic ultrasound skin care design that is commonly shared among all available products in market and in prior arts. The design includes a device body 1, i.e. a handle or a casing. Inside of the device body is the electronics that controls the ultrasound transducer 3 and also provides other functions such as power control and charging. The design also contains a vibration plate 2, which is usually metallic. The vibration plate 2, while being used by a user, contacts the user's or somebody else's skin with its outside surface 4. The vibration plate 2 is driven by an ultrasound transducer 3 at the inside surface at ultrasonic frequency. The vibration from the transducer 3 is transmitted to the skin or skin care products via the driven vibration of the plate 2. The plate 2 and the transducer 3 are contained within the enclosed housing of the device body 1 for easy handling.

Using any of the existing devices, due to the design feature as illustrated in FIG. 1, the user has to dispense the specimen from separate specimen container and applies the specimen either directly to the skin surface or to the surface 4 of plate 2 prior to the treatment on a target skin area. This process of application of skin care specimen from an external container limits the device's portability because it not only increases the complexity of the skin treatment process but also imposes hygiene concerns if such skin treatment process is to be performed not in a dedicated area, such as a beauty salon or a private room, but in a public area with frequent traffic, such as in office, public transportation or elevator.

The inventors realize that ultrasound assistance to skin care specimen effect on skin beautification process is beneficial. However, the effect of ultrasound requires enough application time of the ultrasound vibration on the treated skin area to achieve desired result. For daily beautification purpose, it is desired that such ultrasound treatment process can extend further into a typical user's day time other than the usual limited time skin care process in the morning or at night to benefit from the full scale that ultrasound treatment can offer. Prior arts devices, due to their limited portability and need of separate specimen containment, are unable to meet the stated treatment requirement because of the complexity of the application process.

What is desired is an ultrasonic skin care device with a built-in, replaceable specimen container and a dispensing mechanism to enable easy application of the specimen for skin beautification purpose.

SUMMARY OF THE INVENTION

It is an object of this invention to integrate a skin care specimen dispenser with an ultrasonic vibration generation device to produce a portable and hygiene solution to enable extended ultrasound treatment for daily skin beautification. Another object of this invention is to provide specimen dispenser designs that are feasible to manufacture and user friendly.

The present invention teaches an ultrasonic device with an integrated specimen dispensing system. The device includes a body, a vibrating plate coupled to the body, an ultrasonic generator coupled to the vibrating plate, and an integrated specimen dispensing system. The ultrasonic generator provides ultrasonic vibration in a frequency or frequencies between 20 KHz-25 MHz to the vibrating plate. The vibrating plate has a smooth surface suitable for massaging human skin. The ultrasonic generator and the integrated specimen dispenser are built in the device body. Specimen, such as liquid, gel, or cream, is dispensed to the plate's smooth surface via an outlet coupled to the plate.

The outlet can be a small hole or an array of small holes from which specimen is dispensed. The outlet can be either visible or receded from the vibrating plate's smooth surface such that it is hidden from view.

The integrated specimen dispensing system provides specimen to the vibrating plate's smooth surface via the above described outlet in the smooth surface. The dispensing system may have various implementations, including a refillable cartridge, a disposable cartridge prefilled with specimen, or one or more replaceable containers prefilled with specimen. The dispensing system includes a valve which is sealed when the device is in a non-operation mode or in a mode that a user does not intend to use specimen. The valve is opened or turned on when the user intends to dispense specimen.

In one embodiment where the dispensing system has a multiple identical compartments containing same or different specimen, each of the compartments can be selected and aligned to the outlet. Each of the compartments may include a valve which is sealed when the compartment is not selected by the user.

In another embodiment where the dispensing system has multiple cartridges, each of the cartridges can be selected and aligned to the outlet. Each of the cartridges may have a valve which is sealed when specimen in the cartridge is not selected by the user.

Yet in another embodiment, the outlet comprises a valve which is sealed when the device is in a non-operation mode or in a mode that a user does not intend to use specimen. It is open or turned on when the user intends to dispense specimen.

The dispensing system may include a piston which exerts pressure to specimen contained in a container. The piston can be moved by a force exerted from outside of the container or by a pre-existing force from the container. In an alternative implementation, the dispensing system may include a self-contracting porch which contains specimen and exerts pressure to specimen by the contracting force.

The device has a mechanical leverage structure on the body to control dispense of specimen. The mechanical leverage structure can be a button, a roller wheel, or a lever, with which the user can control the dispensing system manually.

In an alternative implementation, the device has an electrical interface on the body to control dispense of specimen. The electrical interface can be, but not limited to, a switch, a touch sensor, a pressure sensor, or a proximity sensor.

DESCRIPTION OF THE INVENTION

Figure 1:
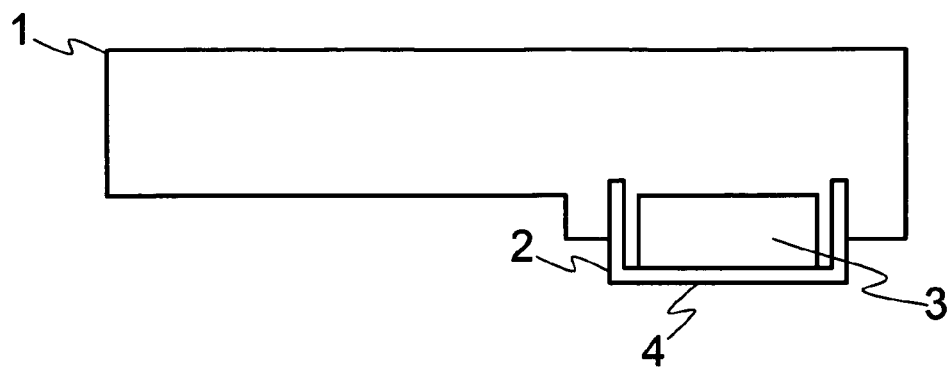
FIG. 1 is a schematic diagram illustrating a generic ultrasound skin care design according to the prior arts.

While the present invention may be embodied in many different forms, designs or configurations, for the purpose of promoting an understanding of the principles of the invention, reference will be made to the embodiments illustrated in the drawings and specific language will be used to describe the same. It will nevertheless be understood that no limitation of the scope of the invention is thereby intended. Any alterations and further implementations of the principles of the invention as described herein are contemplated as would normally occur to one skilled in the art to which the invention relates.

Figure 2A:
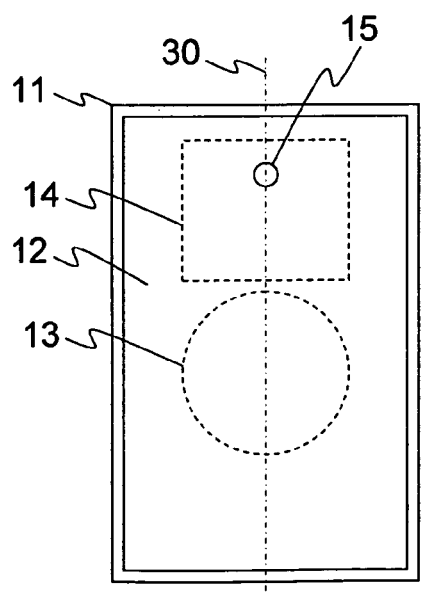
FIG. 2A is a schematic diagram illustrating a front view of an ultrasonic device with an integrated specimen dispenser according to the preferred embodiment of the present invention.
Figure 2B:
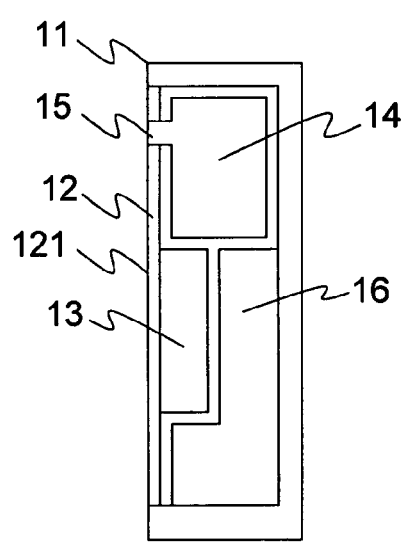
FIG. 2B is a schematic diagram illustrating a cross-section view of the ultrasonic device according to FIG. 2A.

FIG. 2A is a schematic diagram illustrating a front view of an ultrasonic device with an integrated specimen dispenser according to the preferred embodiment of the present invention. FIG. 2B is a schematic diagram illustrating a cross-section view of the ultrasonic device along the center line 30 in FIG. 2A. The device include: (1) an enclosure body 11; (2) an ultrasound transmission plate 12 with its inner side coupled to the body 11 and with its outer side providing a smooth surface suitable for contacting human skin and transmitting ultrasound vibration to the target skin area; (3) an ultrasound generator 13, enclosed in the body 11 and coupled to the transmission plate 12, generating ultrasound vibration with a frequency or frequencies in a range of 20 kHz-25MHz;

(4) a skin care specimen container and dispenser, which are collectively called as a specimen cartridge 14; (5) a specimen outlet 15 located in an upper longitudinal portion of the transmission plate 12, through which skin care specimen is dispensed close to, or preferably directly on, the touching surface 121 of the transmission plate 12 that is to be in contact with the skin during skin treatment; (6) control electronics 16 comprising circuits and components, which controls ultrasonic vibration generation from the generator 13, provides user interface, power supply and charging functions, and optionally, provides specimen dispensing from the cartridge 14. The specimen cartridge 14 is located immediately behind the outlet 15. The generator 13 is located behind a lower longitudinal portion of the transmission plate. The transmission plate's longitudinal measurement is approximately the same as the body's longitudinal measurement and the transmission plate's latitudinal measurement is approximately the same as the body's latitudinal measurement. The plate's longitudinal measurement is larger than its latitudinal measurement. In a typical rectangular configuration, the transmission plate's longitudinal and latitudinal measurements are identical to these of the body 11.

The generator 13, the cartridge 14, and the control electronics 16 are all enclosed in the device body 11. Only outlet 15 is shown on the device surface. In other words, except the smooth surface 121, the outlet 15 is the only physical structure which is visible on the surface 121. Alternatively, the outlet 15 can be receded from the smooth surface of the vibrating plate such that it is hidden from view.

Figure 3A:
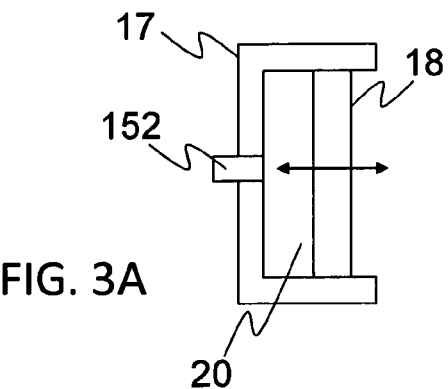
FIG. 3A is a schematic diagram illustrating a first implementation of a specimen cartridge according to the present invention.
Figure 3B:
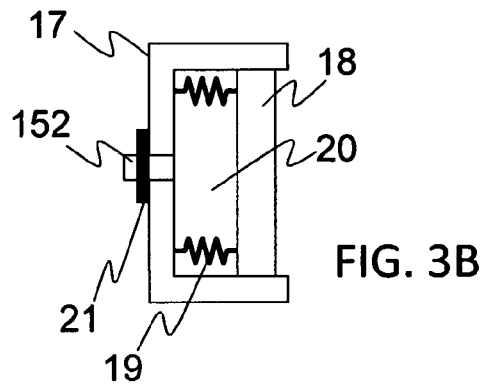
FIG. 3B is a schematic diagram illustrating a second implementation of a specimen cartridge according to the present invention.
Figure 3C:
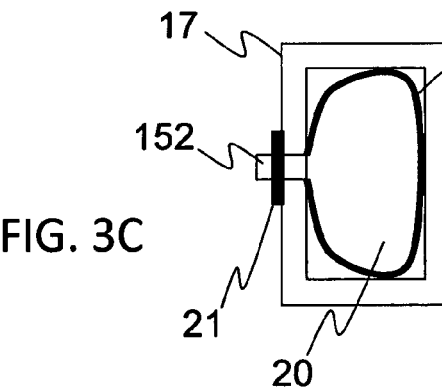
FIG. 3C is a schematic diagram illustrating a third implementation of a specimen cartridge according to the present invention.

FIG. 3A through FIG. 3C are schematic diagrams illustrating the structure and function of the cartridge 14.

FIG. 3A shows a first embodiment of the cartridge 14 having an outside housing 17, an outlet 152 and a piston 18 that moves in the direction towards or away from the interior wall of the housing 17 where the outlet 152 is located. Skin care specimen is stored in the space 20 enclosed by the interior wall and the piston 18. When the piston 18 moves towards the interior wall where the outlet 152 is located and reduces the volume within the space 20, specimen is dispensed through outlet 152 to outside the cartridge 14 due to pressure. Movement of the piston 18 is mechanical, which can be realized through pushing and pulling force from a button-type or a roller-type leverage structures existing externally on the enclosure body 11 of FIG. 2A and FIG. 2B, and thus the specimen dispensing can be manually controlled by the user. Alternatively, the pushing and pulling force can be applied through electric motor component residing within the enclosure body 11 of FIG. 2A and FIG. 2B, and thus the specimen dispensing can be operated by an electrical-switch-type or a touch-sensor-type electronic interface located externally on the enclosure body 11 of FIG. 2A and FIG. 2B.

FIG. 3B shows a second embodiment of the cartridge 14 structure. It is similar to FIG. 3A, but the pushing force is applied by embedded loading force, as exampled by the spring like structure 19 in FIG. 3B. The loading force can be applied from either side of the piston 18, where FIG. 3B is only one of many variations. In addition, the loading force can be implemented as, including but not limited to, spring, rubber cushion, rubber band or compressed air. The loading force applies a constant pressure on the specimen within the space 20, and the specimen can be dispensed through outlet 152 automatically as soon as the outlet 152 is set to an open mode. To control and limit flow of specimen, a switch structure such as a valve 21 is coupled to the outlet 152, which is able to close and open the flow path of specimen through outlet 152. The valve 21 can be a slit valve, a one-way valve, or a double-way valve. Operation of the valve 21 can be realized through a button-type or a roller-type leverage structures existing externally on the enclosure body 11 of FIG. 2A and FIG. 2B, and the specimen dispensing can be operated manually. Alternatively, valve 21 can be operated through an electric motor component residing within the enclosure body 11 of FIG. 2A and FIG. 2B, and thus the specimen can be operated by an electrical-switch-type or a touch-sensor-type electronic interface existing externally on the enclosure body 11 of FIG. 2A and FIG. 2B.

FIG. 3C shows a third embodiment of the cartridge 14 structure. It is similar to FIG. 3B, but replacing the piston and loading structure with a simple self-contracting porch 22 existing within the enclosed housing 17. The self-contracting porch 22 can be, but not limited to, a dilated rubber pocket. The specimen is contained in the internal space of the porch 22. The self-contracting force of the porch 22 produces enough pressure to dispense the specimen when the valve 21 opens up the flow through the outlet 152.

Figure 3D:
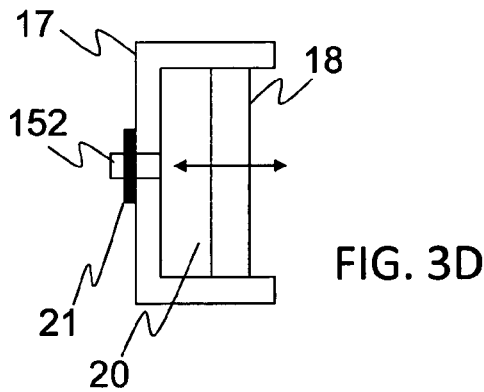
FIG. 3D is a schematic diagram illustrating a forth implementation of a specimen cartridge according to the present invention.

FIG. 3D then shows a fourth embodiment of the cartridge 14 structure. It is a variation of FIG. 3A with a valve 21 coupled to the outlet 152. The valve 21 can be operated simultaneously with the piston 18 to produce more precise specimen flow through the outlet 152. Operation of valve 21 can be achieved through the same mechanical or electronic interface that user uses to operate piston 18.

Dispense of specimen can be controlled by a mechanical device or an electronic interface. The mechanical device can be a button, a roller, a wheel or a lever. The electronic interface can be a switch, touch sensor, pressure sensor, or proximity sensor.

The cartridge 14 may also have any, several or all of the below features: (1) the cartridge 14 is replaceable, i.e., it can be taken out and installed back into the enclosure body 11; (2) cartridge 14 can be reused, i.e., the specimen may be replenished into the space 20 within the cartridge 14 after depletion of the specimen during skin beatification process; (3) the cartridge 14 is pre-filled with specimen and is disposable after the specimen is exhausted; (4) the device may operate without the cartridge 14 installed; (5) two or more cartridges 14 containing same or different specimens may be installed in the enclosure body 11, such that cartridges can be individually selected, positioned and with the cartridge outlet 152 aligned with the outlet 15 of the device body to dispense specimen.

Figure 4A:
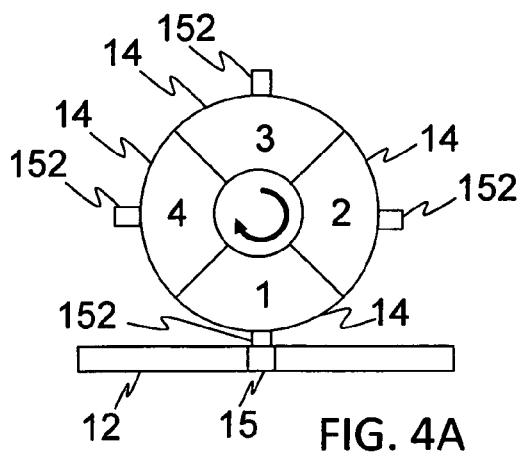
FIG. 4A is a schematic diagram illustrating a rotating design for cartridge selection and positioning in a multiple-cartridge implementation according to the present invention.

The selection, positioning and alignment can be realized by means of, such as but not limited to, a rotation through different cartridges. Different cartridges may have their own built-in specimen dispensing mechanism but share the same user interface for dispensing the specimen when the cartridge is selected and aligned with the outlet 15. FIG. 4A is a schematic diagram illustrating a rotating design for cartridge selection and positioning in a multiple cartridge implementation. In the implementation, there are four cartridges with identical size, body shape and other structural properties. When the user rotates a cartridge to a selection position, the outlet 152 is coupled to the outlet 15 on the transmission plate 12 in a perfect manner.

Figure 4B:
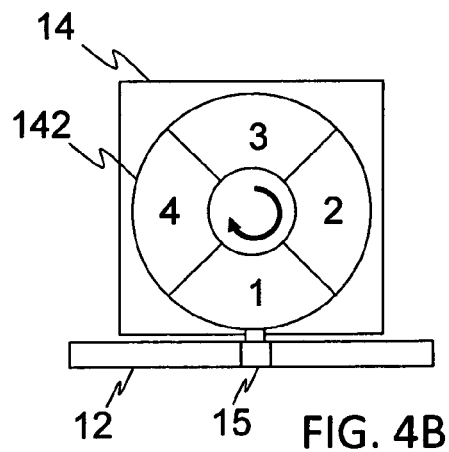
FIG. 4B is a schematic diagram illustrating a rotating design for selection and positioning of cartridge compartment in a one-cartridge with multiple compartment implementation according to the present invention.

The selection, positioning and alignment can be realized by means of, such as but not limited to, a rotation through different compartments or a built-in valve system that defines or designates a compartment from which the specimen is dispensed. FIG. 4B is a schematic diagram illustrating a rotating design for selection and positioning of the cartridge compartment 142 in an implementation of a single cartridge with four compartments. In the implementation, the cartridge 14 has four specimen compartments that contain same or different specimens, such that each compartment within the cartridge can be individually selected, positioned and aligned with the cartridge outlet 152 to dispense specimen. Different compartments may share the same specimen dispensing mechanism as discussed in FIG. 3A through FIG. 3D, or each compartment has its own dispensing mechanism but share the same user interface for dispensing the specimen when the compartment is selected and aligned with the outlet 152.

The advantages of this invention are numerous. For examples: (1) ultrasonic device with integrated specimen dispenser reduces complexity of operation and increases its portability to enable anywhere/any-time usage; (2) multiple specimen containment enables one device for all needed skin treatment process with various specimen options; and (3) disposable cartridge option further increases the easiness and hygiene of specimen application that enables ultrasound treatment of skin to be further extended into daily skin care purpose.

While one or more embodiments of the present invention have been illustrated above, the skilled artisan will appreciate that modifications and adoptions to those embodiments may be made without departing from the scope and spirit of the present invention.

The invention claimed is:

1. An ultrasonic device, comprising:
   a body;
   an ultrasound transmission plate with its inner side coupled to the body and with its outer side providing a smooth surface suitable for massaging human skin;
   an ultrasonic generator which drives said transmission plate by providing ultrasonic vibration in a frequency between 20KHz and 25MHz; and
   means for containing and dispensing specimen to said smooth surface via an outlet in said smooth surface, said means for containing and dispensing specimen to said smooth surface being located immediately behind said outlet;
   wherein said generator and said means are built in the body;
   wherein said outlet is located in an upper longitudinal portion of said transmission plate;
   wherein said generator is located behind a lower longitudinal portion of said transmission plate; and
   wherein said transmission plate's longitudinal measurement is approximately the same as said body's longitudinal measurement and said transmission plate's latitudinal measurement is approximately the same as said body's latitudinal measurement.

2. The device of claim 1, wherein said means comprises any of:
   a refillable cartridge;
   a disposable cartridge prefilled with specimen; and
   one or more replaceable containers prefilled with specimen.

3. The device of claim 1, wherein said means comprises a valve which is sealed when the device is in a non-operation mode or in a mode that a user does not intend to use specimen.

4. The device of claim 1, wherein said means comprises multiple identical compartments, each of which can be selected and aligned to said outlet, wherein said compartments may contain same or different specimen.

5. The device of claim 4, wherein each compartment comprises a valve which is sealed when said compartment is not selected by a user.

6. The device of claim 2, wherein each cartridge comprises a valve which is sealed when specimen in said container is not selected by a user.

7. The device of claim 2, wherein each container comprises a valve which is sealed when specimen in said container is not selected by a user.

8. The device of claim 1, wherein said outlet comprises a valve which is sealed when the device is in a non-operation mode or in a mode that a user does not intend to use specimen.

9. The device of claim 1, wherein said outlet comprises an array of small holes from which specimen is dispensed.

10. The device of claim 1, wherein said outlet is receded from said smooth surface such that it is hidden from view.

11. The device of claim 1, wherein said means comprises a piston which exerts pressure to specimen contained in a container.

12. The device of claim 11, wherein said piston is moved by any of:
- a force exerted from outside of said container;
- a pre-existing force from said container; and
- a contracting force from a self-contracting porch which contains specimen.

13. The device of claim 1, further comprising a mechanical leverage structure on the body to control dispense of specimen, said mechanical leverage structure can be any of: a button, a roller wheel and a lever.

14. The device of claim 1, further comprising an electrical interface on the body to control dispense of specimen, said electrical interface can be any of:
- a switch, a touch sensor, a pressure sensor, and a proximity sensor.

15. The device of claim 1, wherein said specimen is any of: liquid, gel, and cream.

\* \* \* \* \*